(12) United States Patent
Haddadi et al.

(10) Patent No.: US 10,954,954 B2
(45) Date of Patent: Mar. 23, 2021

(54) TURBINE WITH INTERNAL BLADES

(71) Applicant: FINEHEART, Pessac (FR)

(72) Inventors: Mohammad Haddadi, Merignac (FR);
Stéphane Garrigue, Begles (FR);
Arnaud Mascarell, Montbazon (FR)

(73) Assignee: FINEHEART, Pessac (FR)

( * ) Notice: Subject to any disclaimer, the term of this patent is extended or adjusted under 35 U.S.C. 154(b) by 0 days.

(21) Appl. No.: 16/649,573

(22) PCT Filed: Sep. 19, 2018

(86) PCT No.: PCT/EP2018/075358
§ 371 (c)(1),
(2) Date: Mar. 20, 2020

(87) PCT Pub. No.: WO2019/057776
PCT Pub. Date: Mar. 28, 2019

(65) Prior Publication Data
US 2020/0217325 A1 Jul. 9, 2020

(30) Foreign Application Priority Data

Sep. 21, 2017 (FR) ...................................... 1758739

(51) Int. Cl.
A61M 1/10 (2006.01)
A61M 1/12 (2006.01)
F04D 29/18 (2006.01)
F04D 13/06 (2006.01)

(52) U.S. Cl.
CPC ........... *F04D 29/181* (2013.01); *F04D 13/06* (2013.01); *A61M 1/1031* (2014.02); *A61M 1/122* (2014.02); *F05D 2250/25* (2013.01)

(58) Field of Classification Search
CPC .... F04D 27/181; F04D 13/16; A61M 1/1031; A61M 1/122; F05D 2250/25
See application file for complete search history.

(56) References Cited

U.S. PATENT DOCUMENTS

| 5,368,438 A | 11/1994 | Raible |
| 2001/0009645 A1 | 7/2001 | Noda |
| 2008/0292478 A1 | 11/2008 | Baykut et al. |

(Continued)

FOREIGN PATENT DOCUMENTS

| EP | 1481699 | 12/2004 |
| WO | 2007003351 | 1/2007 |

(Continued)

OTHER PUBLICATIONS

French Search Report from French Patent Application No. 1758739, dated Sep. 21, 2017.

(Continued)

*Primary Examiner* — Paula J Stice
(74) *Attorney, Agent, or Firm* — Greer, Burns & Crain, Ltd.

(57) ABSTRACT

A turbine for pumping a fluid includes a body designed to move rotationally, a hollow central part which extends through the body from one side to the other and is intended to allow the fluid to pass through the turbine, and at least one blade that is positioned on the inner wall of the body, in the hollow central part, and is designed to circulate the fluid.

22 Claims, 6 Drawing Sheets

(56) References Cited

U.S. PATENT DOCUMENTS

2014/0341726 A1   11/2014  Wu et al.
2016/0279311 A1*   9/2016  Cecere ................ F04D 29/181
2016/0375187 A1   12/2016  Lee et al.

FOREIGN PATENT DOCUMENTS

| WO | 2009058726 | 5/2009 |
| WO | 2011035927 | 3/2011 |
| WO | 2012112129 | 8/2012 |
| WO | 2017032510 | 3/2017 |

OTHER PUBLICATIONS

International Search Report from International Patent Application No. PCT/EP2018/075358, dated Sep. 19, 2018.

\* cited by examiner

TURBINE WITH INTERNAL BLADES

BACKGROUND

The present invention relates to a turbine for pumping a fluid, in particular but not exclusively a pump for ventricular assistance. The turbine according to the present invention can be used in any system for pumping a fluid.

A turbine according to the invention is a rotary device intended to propel a fluid such as blood or water using energy provided by a motor.

Document WO2017032510 is known, describing a pump equipped with a turbine in an ogive shape. This turbine is equipped with several blades produced on the surface thereof. Despite good performance in operation, such a turbine nevertheless has several drawbacks, like weight and the lack of space for the circulation of the fluid.

The purpose of the present invention is a new turbine reducing the stress on the blood cells.

Another purpose of the invention is to limit friction between the fluid and the turbine.

Yet another purpose of the invention is to reduce the energy consumption of the motor controlling the turbine.

SUMMARY

At least one of these objectives is achieved with a turbine for pumping a fluid, in particular a turbine used for increasing the pressure of the fluid in a pump, this turbine sometimes being referred to as an "impeller".

According to the invention, this turbine comprises:
a body designed to perform rotational movements,
a hollow central part, passing right through the body and intended for the passage of fluid through the turbine, and
at least one blade arranged on the inner wall of the body, in the hollow central part, and designed to cause the fluid to flow.

The object according to the invention is a turbine of a new type, as it is hollow and has internal blades, i.e. directed towards the central axis of rotation. In fact, unlike the known turbines or rotors that generally have a main body with blades arranged on the outer surface, the present invention proposes a hollow turbine with blades produced in the inner surface thereof. The fluid is conveyed through the turbine, on the inside thereof, directly, in a linear flow, with a minimum of friction.

Such an architecture makes it possible to reduce the weight of the turbine with respect to a solid turbine. This makes it possible to improve the comfort of a patient when the turbine is installed in a cardiac pump for example. Furthermore, the electricity consumption is also improved due to the low weight. This results in more compact dimensions of the energy source and/or an improved lifetime for any system using such a turbine.

As the fluid passes inside the turbine, the flow resistance is reduced.

Stress on the blood cells i.e. the shear forces (shear stress), when the fluid is blood, is considerably reduced. Damage to the blood is consequently reduced.

According to an advantageous characteristic of the invention, the blade is of helical type. The function of such a blade is to aspirate the fluid and to make it pass through the inside of the turbine.

This blade can be more or less pronounced, i.e. it can be one or more attached pieces with respect to the turbine or protrusions, grooves or corrugations forming an integral part of the turbine, produced on the inner wall thereof.

The helical blade is like a coil on the inner wall of the turbine, so that the angle of incidence of the helical blade reduces from the upstream end to the downstream end of the turbine; the angle of incidence being defined as the angle between the axis of rotation of the turbine and a vector tangent to the outer surface of the helical blade.

According to another advantageous characteristic of the invention, the turbine comprises several blades distributed on the inner wall of said body. These blades are arranged to apply a minimum of stress to the fluid and to optimize aspiration.

According to an embodiment of the invention, the blade is constituted by several turns with an increasing winding pitch that tends towards infinity.

In an embodiment, the turbine according to the invention can comprise a rod arranged along the central axis so as to reduce the backflow of fluid.

The rod can advantageously be fixed. Although this does not constitute a preferred embodiment, it is nevertheless possible to envisage a rotating rod, firmly fixed to the turbine or not, fixed to the inlet chamber or not.

For example, this rod can be fixed to said at least one blade or to the body of the turbine or by one end to an inlet chamber which can be firmly fixed to a casing around the turbine. When the rod is fixed to the inlet chamber, it is fixed and the turbine can revolve about it.

The function of this rod is to contribute to stopping any reflux of blood and preventing the creation of vortices.

Advantageously, the hollow central part of the turbine can have a cylindrical shape. That is to say that the inner wall of the turbine can have the profile of a right cylinder, with a circular cross section for example, and/or the fixed or variable radial thickness of the blade is such that the void (filled with air or fluid) has the profile of a right cylinder, with a circular cross section for example.

According to an embodiment of the invention, the hollow central part can have a flared shape, the more open end being arranged downstream in the direction of flow of the fluid.

The outlet orifice of the turbine is larger than the inlet orifice.

According to another embodiment of the invention, the hollow central part of the turbine has an oblong shape, the more open end being arranged downstream in the direction of flow of the fluid.

Preferably, for efficient rotation, the body of the turbine can have an outer shape of the right cylinder type with a circular cross section.

Advantageously, permanent magnets can be incorporated into said body. These magnets make it possible to use the turbine as the rotor of an asynchronous motor, for example.

According to an embodiment, the radial thickness of the blade can be fixed or variable over the entire length between the upstream end and the downstream end of this blade, i.e. over the entire length of the blade. If it remains constant, the blades then delimit a zone which has a shape substantially identical to the shape of the hollow part.

According to an advantageous characteristic of the invention, the hollow central part and said at least one blade having a profile of centrifugal type on the upstream side, mixed-flow type in the central part, and axial type on the downstream side.

With the pump according to the invention, the turbine is capable of providing a pump incorporating at the same time the characteristics of:

a pump of centrifugal type, i.e. radial acceleration for the portion of the fluid caught by the blades and arriving axially; to this end, the lower part of the blades, in particular helical, can have a pronounced angle, of the order of 45 degrees, for example between 40 and 50 degrees, with respect to the axis of rotation of the turbine, a pump of mixed-flow type, i.e. a less pronounced slope or curve of the turns of the helical blades for example, and a pump of axial type, the fluid being channelled in a direction parallel to the axis of rotation of the turbine.

This configuration makes it possible to limit the shear stress which can cause hemolysis, i.e. destruction of the red blood cells. Even with a high flow rate, when red blood cells are destroyed, oxygen does not reach the cells.

Shear stresses are created by the effects of blood swirling at the inlet and outlet of the pump. The pump according to the invention avoids vortices via suction of blood using a structure of the centrifugal type and an axial delivery.

According to an advantageous characteristic of the invention, a first zone of said at least one blade is dimensioned so that the fluid reaches a specific speed comprised between 0 and 1.2 RPM; this first zone being on the upstream side of the blade.

Furthermore, a second zone of said at least one blade is dimensioned so that the fluid reaches a specific speed comprised between 1 and 2.2 RPM; this second zone being at the level of the middle of the blade.

Finally, a third zone of said at least one blade is dimensioned so that the fluid can reach a specific speed greater than 2.2 RPM; this second zone being on the downstream side of the blade. This is a specific speed value making it possible to classify the centrifugal, mixed-flow or axial structures respectively.

According to another aspect of the invention, a pump is proposed, designed for the circulation of a fluid, this pump comprising:

a casing, and a turbine arranged in the casing and designed to perform rotational movements relative to the casing.

According to the invention, the turbine comprises:

a body designed to perform rotational movements, a hollow central part, passing right through the body and intended for the passage of fluid through the turbine, and at least one blade arranged on the inner wall of the body, in the hollow central part, and designed to cause the fluid to flow.

The pump according to the invention incorporates the new turbine described above, thus benefiting from the advantages established for this turbine. The pump according to the invention can also operate with a very low noise level.

Advantageously, the casing and the turbine can constitute a part of a brushless motor, the casing having the stator function and the turbine having the rotor function. Thus a synchronous machine is constituted, with permanent magnets arranged in the rotor, while stator coils (windings) are produced in the casing used as stator. In this embodiment, the control electronics is provided and arranged in such a way as to act on the windings.

According to another embodiment of the invention, the pump can comprise a motor external to the turbine and driving a transmission shaft, the latter being arranged along the axis of rotation of the turbine and firmly connected to the turbine by at least one radial rib. Unlike the preceding case where the motor was finally incorporated, in the present embodiment, the motor is external to the turbine and comprises a shaft which drives the turbine in rotation. The shaft is firmly fixed to the turbine by ribs which have a profile allowing easy passage of the fluid.

Preferably, the transmission shaft can be connected at both the upstream end and the downstream end of the blade.

According to an advantageous characteristic of the invention, the pump also comprises:

an inductor equipped with guide vanes to make the flow of the fluid linear; this inductor being arranged upstream of the turbine with respect to the direction of flow of the fluid;

a diffuser equipped with diffusion vanes in order to make the flow of fluid linear and increase the pressure of the fluid; this diffuser being arranged downstream of the turbine so as to evacuate the fluid outwards from the turbine, converting the kinetic energy created by the turbine into potential energy; and a straightener equipped with straightener vanes and an outlet orifice having a diameter less than the inlet diameter of the straightener, the straightener vanes directing the fluid from the diffuser to the orifice so as to increase the speed and give the fluid a predefined profile when leaving the orifice.

The linear flow of fluid such as defined here is linear by comparison with a swirling flow. This linear flow can be laminar.

The straightener according to the invention makes it possible to create a flow by concentrating the fluid so as to obtain high speed values at the outlet of the pump. In general, the vascular system of a heart has fairly high circulatory resistances. An efficient pump is a pump that is capable of propelling the blood in the valves with sufficient pressure to overcome these circulatory resistances. The pump outlet pressure is paramount in comparison to the outlet speed, which with the pump according to the invention can reach the maximum speed of 3 m/s.

In other words, the straightener makes it possible to channel the fluid, to create a profile making it possible to have a maximum speed at a point, i.e. aligned with the aortic valve, so as to expel the flow in a laminar fashion. This makes it possible to avoid the creation of vortices at the outlet of the pump. The diameter of the outlet orifice is smaller than the internal diameter of the casing. The smaller outlet diameter thereof, for example half or a third of the internal diameter of the casing, makes it possible to adjust the pressure parameters, between 80 and 200 mmHg, and the speed parameters, between 1 and 3 m/s, while avoiding the creation of a flow with negative speed (backflow due to lack of pressure and homogeneity of the outlet flow).

The diffuser and straightener assembly according to the invention thus makes it possible for the pump to be made efficient. The straightener distributes the fluid directly towards the outlet in the ambient medium by creating a flow therein. This ambient medium can advantageously be said fluid, which is preferably blood.

The inductor according to the invention avoids the phenomenon of cavitation, i.e. the creation of vapour bubbles in the fluid.

It is important to note that this pump is perfectly suitable for operation in a vertical arrangement, or slanting slightly, i.e. inclined between 0 and 5 degrees with respect to the vertical axis. The pump according to the invention can also operate lying down, like most of the pumps of the prior art.

The pump according to the invention can also comprise an inlet chamber equipped with side openings so that the fluid can enter radially then engage axially towards the inductor.

This inlet chamber can have a cylindrical shape comprising, on its upper part downstream of said openings, a receptacle for housing the inductor. The inlet chamber and the inductor can constitute two parts intended to be firmly fixed to one another or be designed as one and the same piece. The casing can also be combined with them so as to constitute a single piece.

BRIEF DESCRIPTION OF THE DRAWINGS

Other advantages and characteristics of the invention will become apparent on examination of the detailed description of an embodiment that is in no way limitative and from the attached drawings, in which.

DETAILED DESCRIPTION

The embodiments which will be described hereinafter are in no way limitative; in particular variants of the invention may be implemented comprising only a selection of the characteristics described hereinafter, in isolation from the other characteristics described, if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

In particular, all the variants and all the embodiments described are intended to be combined together in any combination, where there is no objection on technical grounds thereto.

In the figures, elements common to several figures retain the same reference.

Figure 1:
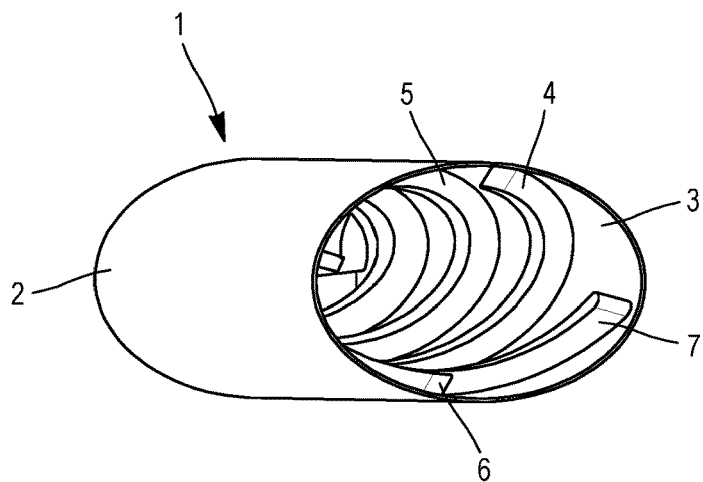
FIG. 1 is a diagrammatic view of a turbine with internal blades according to the invention.

FIG. 1 shows a turbine 1 according to the invention. In the example, described non-limitatively, this is a body 2 in the shape of a slender hollow cylinder the inner wall 3 of which comprises several blades 4, 5, 6 and 7. Such a turbine can advantageously be used in a pump immersed in a fluid.

The function of the blades is to convey the fluid through the turbine. The orientation and dimensioning of the blades are provided so that the fluid is aspirated then propelled after having passed through the turbine when in rotation.

Unlike the systems of the prior art where the fluid flows on the outside of the turbine, the present invention proposes a hollow turbine making the fluid flow on the inside.

Figure 2A:
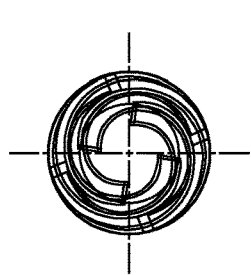
FIGS. 2a, 2b and 2c are diagrams showing the arrangement of the helical blades inside the turbine according to the invention.
Figure 2B:
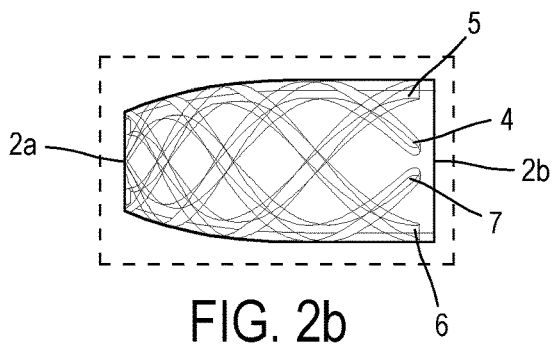

FIG. 2b shows the four helical blades 4 to 7, which start from one end of the turbine, lie in helical lines without ever crossing one another, and arrive at the other end.

Figure 2C:
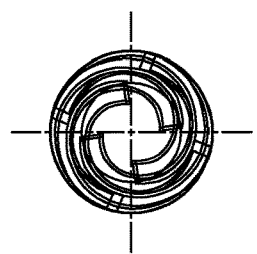

In the example in FIG. 2b, the hollow central part of the body 2 has a concave flared shape. The upstream end 2a has a smaller opening than the downstream end. FIG. 2a is a front view of the end 2a while FIG. 2c is a front view of the end 2b. The helical blades follow the shape of the inner wall 3.

Figure 3A:
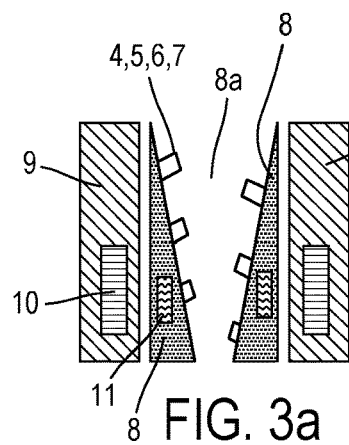
FIGS. 3a, 3b and 3c are diagrammatic cross section views showing a brushless DC motor in different configurations of the hollow central part of the turbine according to the invention.
Figure 3B:
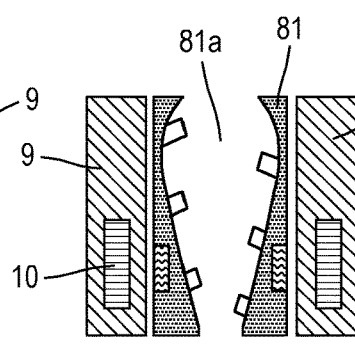
Figure 3C:
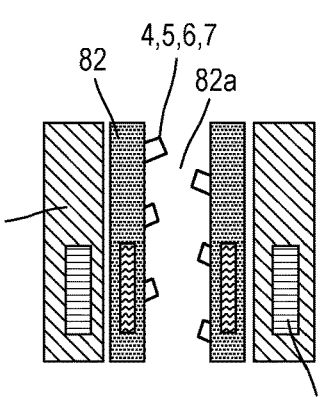

The hollow central part can have other shapes like those shown non-limitatively in FIGS. 3a to 3c.

A turbine 8 is shown in cross section in FIG. 3a. This is a cylinder having a flared hollow central part 8a shaped like a funnel. A blade 4 is shown diagrammatically. Of course, several blades 4, 5, 6 or 7 can be arranged. This turbine 8 is designed to rotate with respect to a surrounding casing 9. Ideally, the casing 9 is a stator comprising magnetic windings 10. These latter can work together magnetically with permanent magnets 11 arranged on the inside or the outer surface of the turbine. Electronic means (not shown) are provided for controlling the windings 10 so as to actuate the turbine. The assembly constitutes a motor of the brushless type. The gap between the turbine and the casing is straight, it lies within a right cylinder, but it can have another shape that is not straight, flared or not.

In FIG. 3b, the hollow central part 81a has an oblong shape as in FIG. 2b, but with a slightly closed-in downstream end.

In FIG. 3c, the hollow central part 82a has the shape of a right cylinder.

The three FIGS. 3a, 3b and 3c have the same casing 9 as well as the same magnetic elements allowing a motor of the brushless type to be constituted.

Figure 3D:
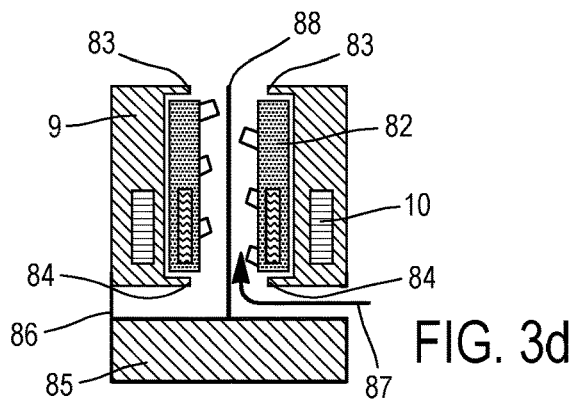
FIG. 3d is a diagrammatic cross section view showing a motor of the type of those set out in FIGS. 3a to 3c with a rod arranged at the centre of the turbine.
Figure 3E:
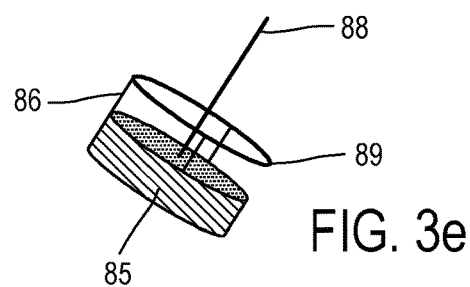
FIG. 3e is a diagrammatic view of an inlet chamber bearing the rod in FIG. 3d.

It has been noted that the arrangement of a rod inside the turbine makes it possible to improve blood flow when the pump is in operation, i.e. the turbine in rotation with respect to the casing. FIG. 3d shows an embodiment of a pump in which a straight rod 88 is axially arranged in the turbine. In the example shown in FIG. 3d, the pump comprises an inlet chamber which can be seen in FIG. 3e. This inlet chamber comprises a base 85 bearing bridging pieces 86 linked to a ring 89 for fastening to the casing 9. The passages between the ring 89 and the base 85 allow the entry 87 of the fluid or the blood towards the inside of the turbine along the rod 88, under the action of the blades 4, 5, 6, 7. This rod 88 can have a height such that the free end thereof (upper in FIG. 3d) is located inside the turbine, beyond the turbine, flush with the upper end of the turbine or the casing.

The rod 88 is fixed by one end to the base 85. Other arrangements of the rod can be envisaged, such as for example connected to the turbine only and no longer to the base 85. In fact, the rod 88 can be fixed to the body 82 of the turbine or to one of the blades 4, 5, 6, 7 for example at the top, at the upper end (with respect to the representation in FIG. 3d). In this case, the lower end of the rod 88 can preferably be free or fixed to a blade, to the body of the turbine or to the inlet chamber.

In particular, in addition to the above and in a manner compatible with other embodiments, the turbine can be contained within the casing by means of flanges 83 and/or 84 produced for example at the ends of the casing and extending inwards. Roller bearing mechanisms can be provided between the turbine and the flanges. Other means can be provided to hold the turbine in rotation in the casing without contact. In particular, a mechanism can be envisaged using levitation, a fluid, magnetism, etc. with or without the flanges 83 and/or 84.

FIGS. 1 to 3 set out in particular a turbine and a casing which, combined with the components for inlet and outlet of fluid and electronic components, make it possible to constitute a pump.

A pump according to the invention, incorporating a turbine as described above, will now be described with reference to FIGS. 4 to 6.

Figure 4:
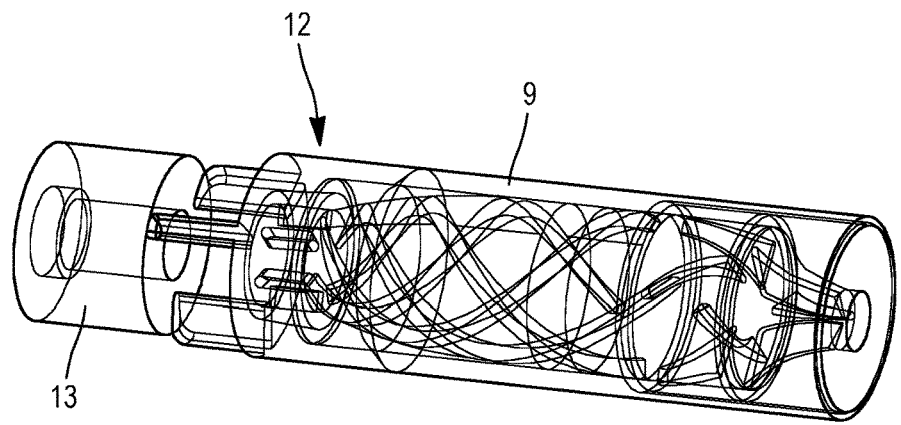
FIG. 4 is a transparent diagrammatic view of the inside of a pump incorporating a turbine according to the invention.

FIG. 4 shows a transparent overall view of a pump 12. This pump has the overall shape of a cylinder with a circular cross section, intended to aspirate a fluid such as blood and deliver it so as to promote blood circulation. Such a pump is intended to be installed in a body, in particular for ventricular assistance. The length thereof is approximately 61.8 mm, the diameter of the casing 9 is approximately 17-20 mm, while the lower part 13 has a diameter of approximately 15-20 mm.

The pump according to the invention can advantageously, but not exclusively, be used in a vertical position, i.e. with the casing 9 vertical and above the lower part 13. The lower part 13 is an inlet chamber.

According to the invention, the function of the inlet chamber 13 is to allow fluid, in particular blood, to enter via the inlets or openings 13a under the action of aspiration originating from inside the casing 9. The fluid is then delivered via an opening at the upper end of the casing.

The upper stages of the inlet chamber 13 comprise the turbine 1 intended to rotate inside the casing 9, and outlet elements such as a diffuser 14 and a straightener 15. The turbine 1 shown in the exploded view in FIG. 5 has a hollow central part, oblong, oval or ogival in shape, elongated or extended on one end. The hollow central part delimited by the inner wall 3 has a diameter of the circular cross section (radial section) that increases from the lower part thereof to the upper part.

Figure 5:
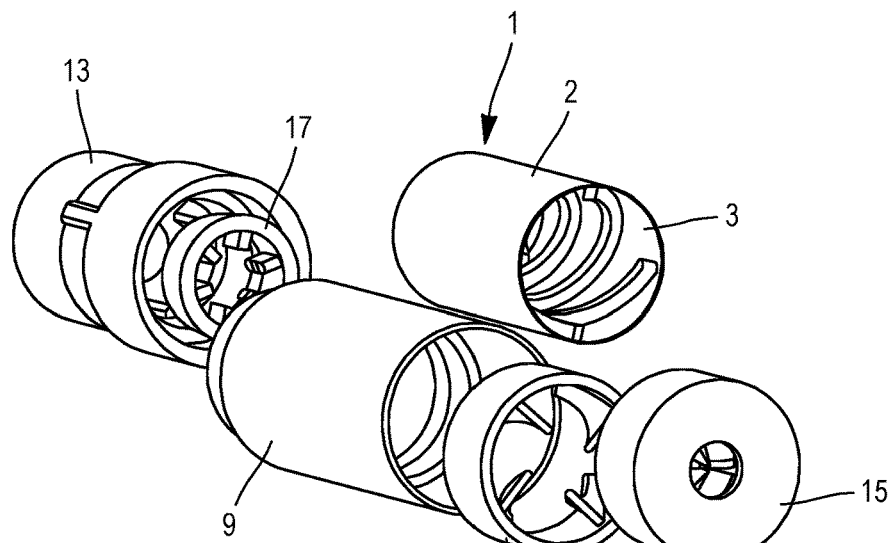
FIG. 5 is an exploded view of the pump incorporating a turbine according to the invention.

In FIG. 5, the exploded view makes it possible to understand that the two components shown externally overall are the casing 9, having a smaller lower part intended to be inserted into the upper part of the inlet chamber 13. The turbine 1 is inserted inside the casing 9, in the central part. The diffuser 14 and the straightener 15 are nested in the casing 9 by the upper end.

Figure 6:
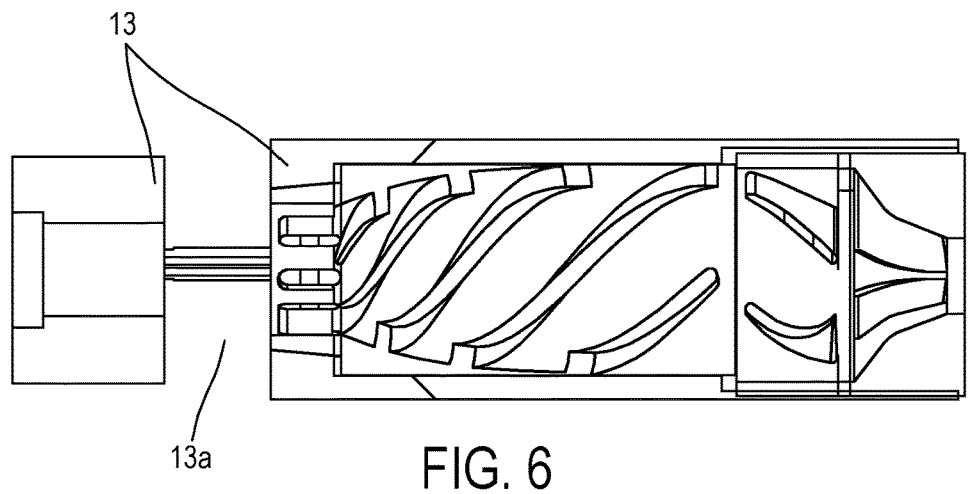
FIG. 6 is a view in cross section of the pump in FIGS. 4 and 5.

FIG. 6 clearly shows the helical blades produced on the inner wall 3.

The different parts of the pump can be designed for moulding, 3D printing, machining, or other means. Advantageously, between three and five blades are produced.

Figure 7:
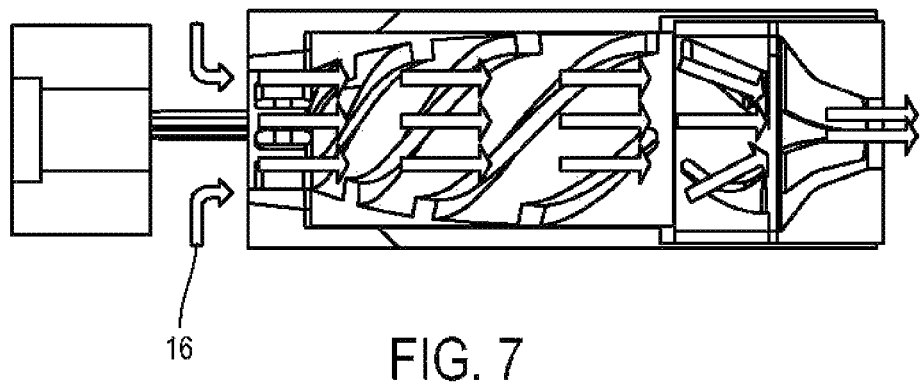
FIG. 7 is a longitudinal diagrammatic view in cross section of a pump according to the invention.

In FIG. 7, arrows 16 indicate the path of the fluid inside the pump. The fluid enters via openings 13a in the inlet chamber, and is then axially accelerated in the turbine under the rotary action of the blades. Each helical blade is a coil the thickness of which is constant or variable over the entire length so that the shape of the inner space conforms to the shape of the inner wall 3, or not. This inner shape is oblong or of the ogival type.

The axial turbine according to the invention is provided for continuous operation.

Fluid circulation takes place in a linear flow which occupies the entire central space of the turbine. The flow rate is thus significant, and in particular when it is blood, the fluid undergoes the smallest possible impact, therefore the least possible stress on the cells.

Figure 8:
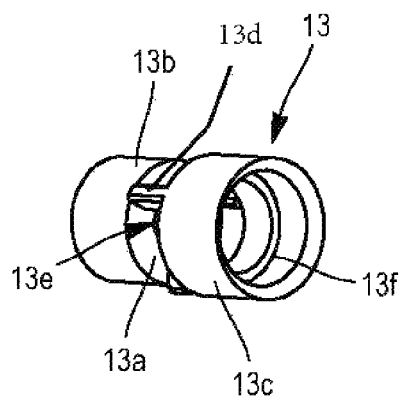
FIG. 8 is a perspective view of an inlet chamber according to the invention.

FIG. 8 shows the inlet chamber 13 in greater detail, constituted by a lower part 13b, an upper part 13c, the two parts being connected by radial guides 13d delimiting the openings 13a towards the inside of the inlet chamber.

The lower part 13b is a cylinder with a circular cross section, having a thick wall, such that the central part is a tunnel 13e. In the example in FIG. 8, the diameter of the tunnel is 6 mm.

The radial guides 13d are three plates lying within planes that intersect at the axis of the inlet chamber. The outer face of each plate 13d is flush with the lateral outer surface of the upper part 13c. The central zone of the upper part containing the axis of the inlet chamber is void for passage of the fluid. This central zone constitutes a tunnel having a diameter greater than the diameter of the tunnel 13e.

Figure 9:
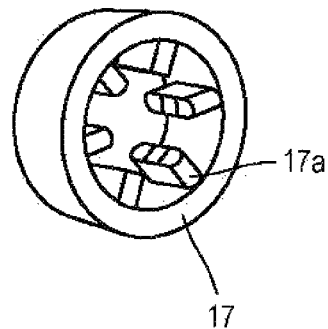
FIG. 9 is a perspective view of an inductor to be inserted in the inlet chamber according to the invention.

The upper part 13c is in the form of a cylinder, having two different thicknesses, a first thickness on the upstream side, i.e. on the side in contact with the radial guides 13d, and a second thickness, smaller than the first, on the downstream side. A step 13f is located between the two thicknesses. With such an arrangement, an inductor 17 as set out in FIG. 9 can be inserted and fixed to the inside of the inlet chamber 13 in the part 13c of great thickness. During insertion, this inductor 17 can be fitted on the ends of the guides 13d. The dimensions of the inductor 17 are such that once inserted, the upper part thereof is flush with the step 13f. Other embodiments can be envisaged, such as for example a single piece constituted by elements 13c and 17, or 13 and 17. The inductor 17 is a hollow cylinder comprising radial guides 17a, for example from four to six in number, over the entire height of the cylinder and lying in radial planes converging at the centre of the cylinder. The inductor 17 acts as a fluid intake guide. It makes it possible to limit cavitation in the upper stages. The guides 17a produce a laminar flow such that the turbulent nature of the fluid is reduced considerably. This makes it possible to slow and reduce deterioration of the turbine, which is generally rapid, by limiting repeated impact of the fluid on the blades of the turbine.

It will be noted that only the upper part 13c of the inlet chamber can be combined with the rest of the pump when the casing and the turbine constitute a brushless motor.

Figure 10:
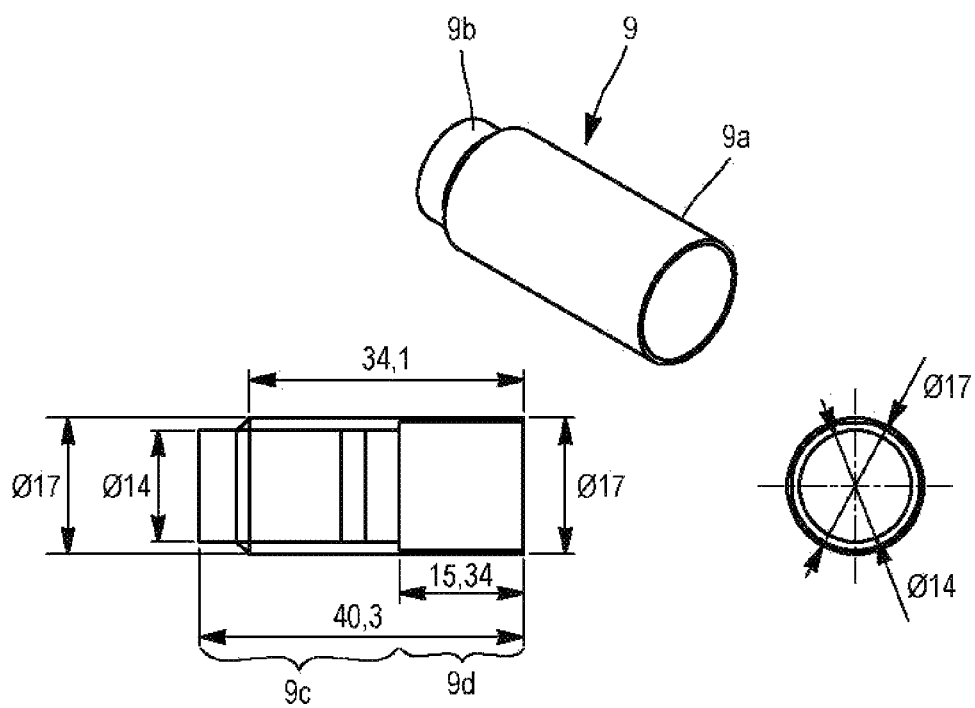
FIG. 10 shows different views in cross section and in perspective of a casing intended to contain the turbine according to the invention.

FIG. 10 shows the casing 9 in greater detail, constituted by a main body 9a and a secondary body 9b. The main body 9a is an elongated cylinder, the secondary body being a cylinder the outside diameter of which is less than the outside diameter of the main body. The secondary body 9*b* is shaped so as to be inserted and held fixed within the upper part 13*c* of the inlet chamber.

Preferably, the lower end of the secondary body 9*b* abuts the step 13*f*, shown in FIG. 8.

The inner shape of the casing 9 is complementary to the outer shape of the turbine, with a gap between them. The upper end 9*d* of the casing 9 comprises an internal diameter greater than the diameter of the lower part 9*c*; the lower part housing the turbine. The diffuser 14 and the straightener 15 are housed in this upper part 9*d* of the casing 9. The turbine therefore does not occupy the entire length of the casing. The turbine can be held in the casing by using bearings and seals.

By means of the specific shape thereof, the turbine according to the invention allows kinetic energy to be imparted to the fluid. It adjusts the speed of the fluid without shear, also increasing its pressure. To this end, the outlet elements of the pump contribute towards increasing the pressure by having a small outlet orifice as well as specific shapes.

Figure 11:
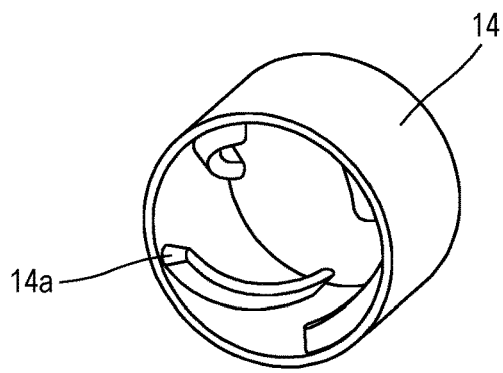
FIG. 11 is a perspective view of a diffuser according to the invention.

FIG. 11 shows the diffuser 14 which is a cylinder intended to cap the head of the turbine. The diffuser comprises guide blades 14*a* oriented in the direction of outflow of the fluid driven by the turbine. The orientation of the guide blades makes it possible to convert a portion of the kinetic energy of the fluid into pressure, which is potential energy. The thickness of the guide blades can be stable along the diffuser, or can be variable.

Figure 12:
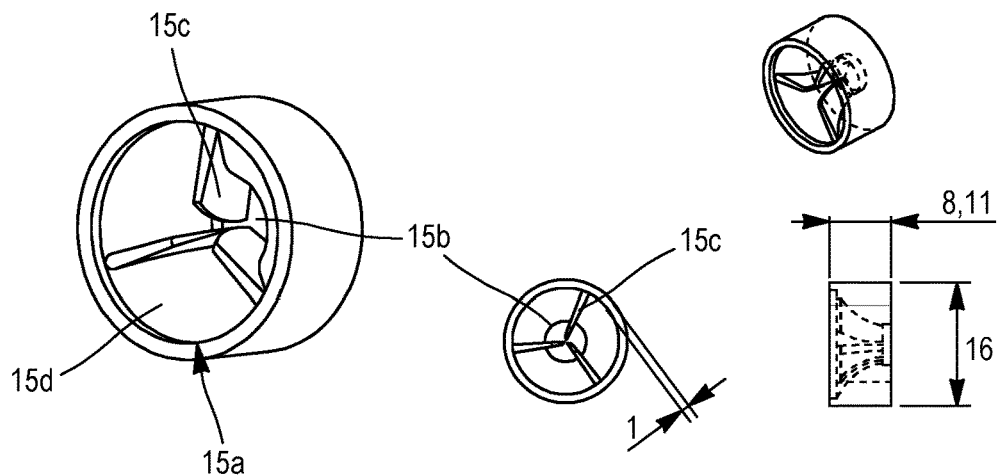
FIG. 12 is a perspective view of a straightener according to the invention.

FIG. 12 shows a straightener 15, the purpose of which is to guide the outflow of the fluid by creating a laminar flow so as to eliminate all turbulence. This is a cylinder 15*a* open at its base to receive the fluid originating from the turbine via the diffuser 14. It comprises an orifice 15*b* having a smaller diameter with respect to the diameter of the opening 15*a* on its base.

An inner wall 15*d* can be seen, having a concave conical shape from the opening 15*a* over its first half, then convex conical over its second half towards the orifice 15*b*. The fluid is pressurized when pushed towards the small-diameter orifice.

Three guide blades 15*c* can also be seen, lying within radial planes that converge at the centre of the straightener. Each blade is a plate the width of which is thicker on the side of the wall than on the side of the centre of the cylinder. The width then reduces as the distance from the wall of the cylinder increases.

In the configuration described, for each guide blade, the profile of the side facing the axis of rotation of the cylinder is curved, in particular in an arc of circle, such that the guide blades are closer to one another at the level of the orifice and are further away on the side of the opening 15*a*.

The turbine 1 according to the invention, with the casing 9 and electronic and magnetic elements, forms a brushless motor capable of making the fluid flow.

Figure 13:
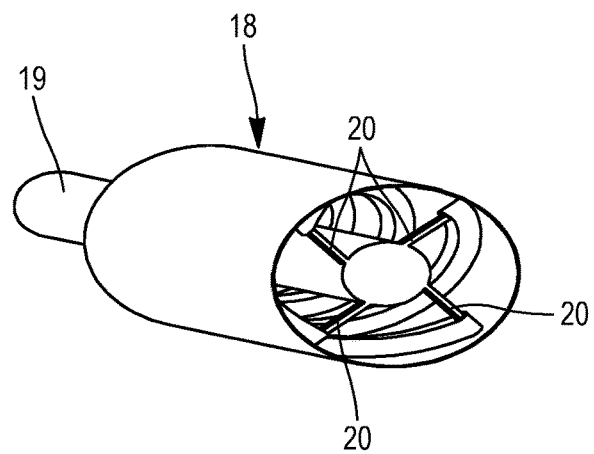
FIG. 13 is a perspective view of a turbine fixed to a transmission shaft of a motor according to the invention.

Another turbine 18 according to the invention is shown in FIG. 13. This turbine 18 can be identical to the turbine 1 described above, with or without magnetic components (windings and permanent magnets and any other element allowing a motor to be constituted). When it does not comprise permanent magnets, the body of the turbine can have a lighter and more slender design.

Figure 15:
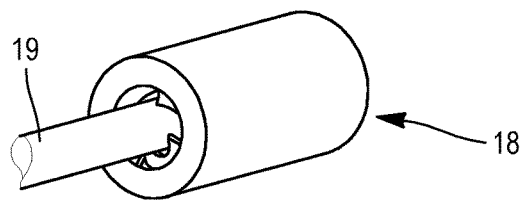
FIG. 15 is a diagrammatic view showing a fastening between a transmission shaft and the turbine in FIG. 13 according to the invention.

The particular difference with the turbine 1 is the presence here of a transmission shaft 19 which is fixed to the turbine 18. This transmission shaft 19 is inserted into the axis of the turbine 18 and has a greater length such that it extends beyond the turbine through the lower (upstream) part and does not extend beyond the upper (downstream) end of the turbine. The upper end of the transmission shaft 19 comprises four ribs or rods 20, each connected at the end of a blade. As shown in FIG. 15, provision is also made for the transmission shaft to be fixed at the level of the lower (upstream) end of the turbine 18, directly or via ribs at the lower ends of the blades. In this way, the transmission shaft is solidly connected to the turbine, the rotation of this shaft causing the turbine to rotate. This shaft 19 can be the transmission shaft of an external motor or an independent rod capable of engaging with a motor.

Figure 14:
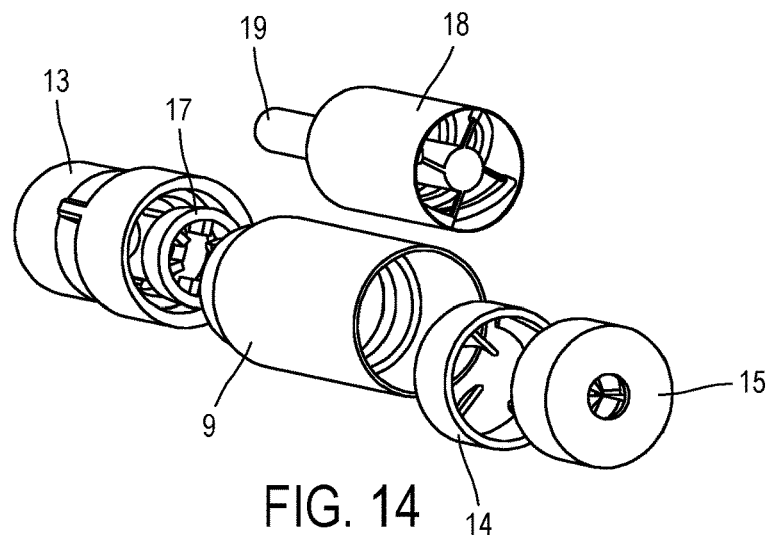
FIG. 14 is an exploded view of the pump incorporating the turbine in FIG. 13 according to the invention.

FIG. 14 is an exploded view in which the same elements are shown as in FIG. 5, but with a turbine 18 replacing the turbine 1. The transmission shaft passes through the axis of revolution of the inductor 17 and of the inlet chamber 13. The casing 9 can also be different, more simplified, when it has no magnetic windings for constituting a stator.

Control of a turbine 18 and a casing 9 can be envisaged both by an external motor via the transmission shaft 19 and by an asynchronous or brushless motor constituted by the turbine 18 and the casing 9. It should be noted that the external motor can also advantageously be the brushless type.

Figure 16:
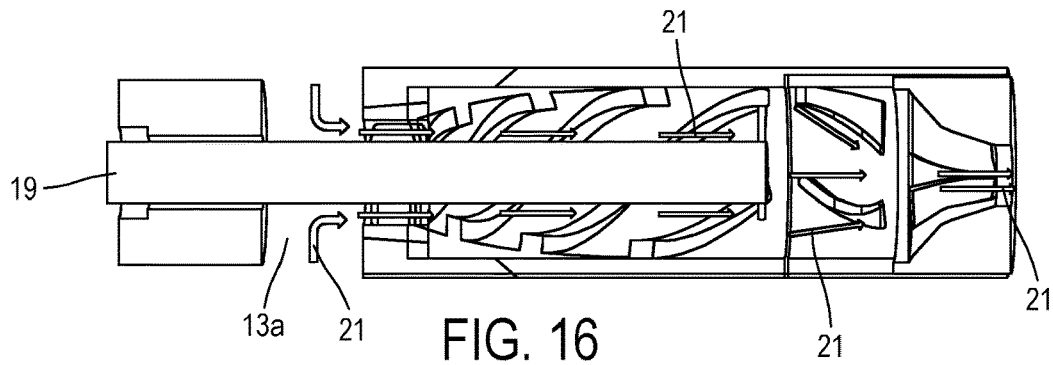
FIG. 16 is a diagrammatic cross section view exposing the inside of a pump incorporating the turbine in FIG. 13 according to the invention.

In FIG. 16, the arrows 21 represent the flow of the fluid such as blood inside the pump. The blood arrives radially through the openings 13*a* of the inlet chamber, then is orientated axially along the transmission shaft 19 via the inductor 17, the transmission shaft being in rotation as well as the turbine 18. The blood is then evacuated via the diffuser 14 and the straightener 15.

The blood flow is then evacuated towards the outside, passing through the diffuser 14 and the straightener 15 which by means of its outlet orifice creates a high-pressure laminar flow. Provision is made for the pump to operate under immersion at a frequency ranging from 500 to 10,000 rpm.

Figure 17:
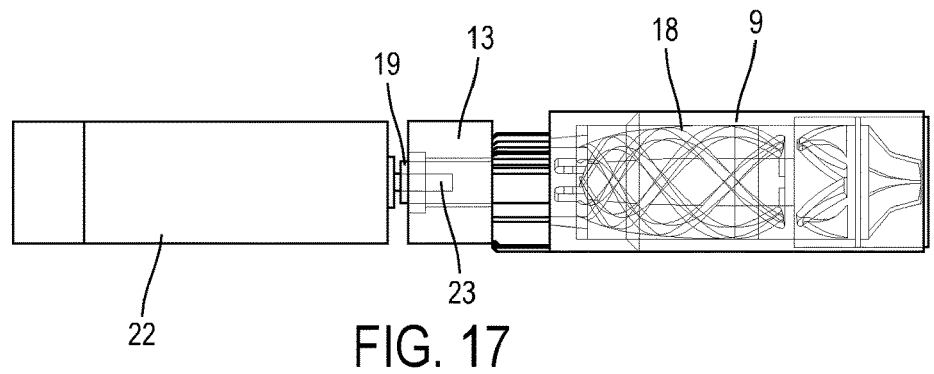
FIG. 17 is a diagrammatic view of a pump according to the invention comprising a motor the transmission shaft of which is connected to the turbine in FIG. 13 according to the invention.

FIG. 17 shows a pump according to the invention incorporating the turbine 18 as well as an external brushless motor 22. The latter is firmly connected to the transmission shaft 19 by means of a drive shaft 23. Preferably, this connection is detachable, so that it is possible to replace the motor easily in the event of failure. This can be a connection by clip, screwing or other. This connection can also be the only joint between the motor and the rest of the pump.

Figure 18:
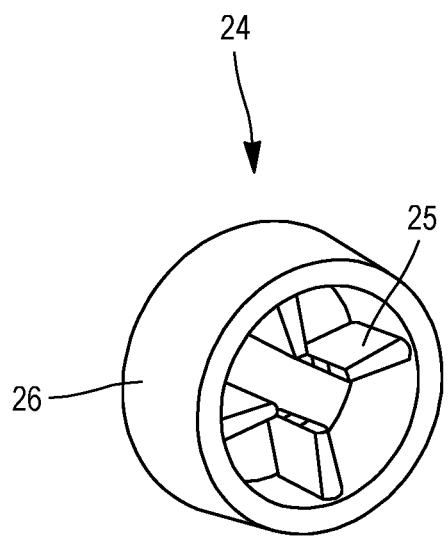
FIGS. 18 and 19 are diagrammatic views of an inductor according to the invention.
Figure 19:
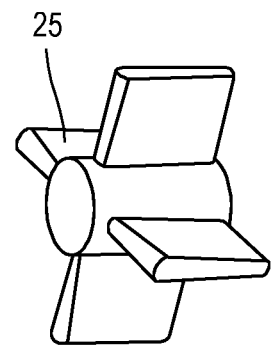

FIGS. 18 and 19 show a diagrammatic representation of an individual inductor 24 in FIG. 18 and a diagrammatic representation of the blades 25 only of this inductor in FIG. 19. This inductor can be individually designed. It will then be fixed firmly in an inlet chamber. It can also be directly produced in an inlet chamber or in a turbine enclosure; in this case the blades are produced on the inner wall of the inlet chamber or the turbine enclosure. The central zone of the inductor is left free for the passage of the fluid. In FIG. 19, the central zone of the inductor represents the flow of the fluid.

Generally, and for all of the embodiments, the blades of the inductor according to the invention are thicker upstream than downstream in the direction of displacement of the fluid. The thickness progression can be linear, but preferably discontinuous: a linear progression until a certain thickness is reached, then the thickness remains constant over the remaining length of the blade. Furthermore, the blades can also be thicker at the point of connection with the cylinder 26 which bears them than at the central end. Provision is also made for an angle between the radial section of each blade and the radius of the cylinder 26 bearing the blades.

Figure 20:
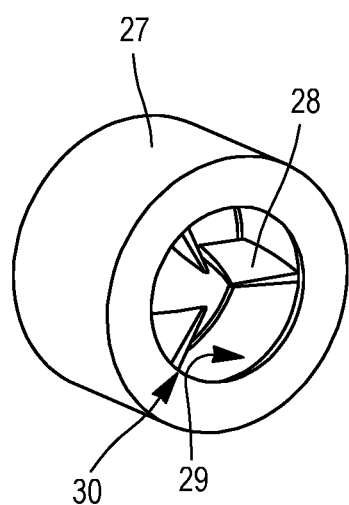
FIGS. 20 and 21 are diagrammatic views of a straightener according to the invention.
Figure 21:
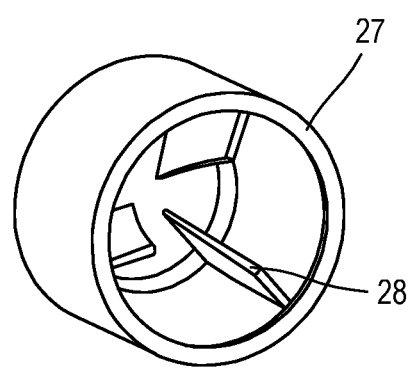

FIGS. 20 and 21 show a front view and a rear view of a straightener according to the invention. This straightener can be produced individually then fixed in the casing of the pump or directly produced on the inner wall of the casing, i.e. a wall shaped identically to the inner wall of the cylinder 27 of the straightener and the blades designed directly on this wall. The blades 28 are thicker upstream than downstream in the direction of flow of the fluid. The thickness progression can be linear. FIG. 20 shows the downstream side of the straightener, i.e. the point through which the fluid is outlet. FIG. 21 shows the upstream side of the straightener, the fluid inlet. On this latter side, the blades 28 leave a central space larger than that of the downstream side, the blades and the inner wall 29 of the cylinder 27 bearing the blades being designed so as to guide the fluid to the outlet orifice 30 which is narrower than the inlet of the straightener.

Of course, the invention is not limited to the examples which have just been described and numerous modifications may be made to these examples without departing from the scope of the invention.

The pump according to the invention can easily be implanted in a heart due to its small dimensions, on account of its particular design allowing high pressure while preserving the quality of the blood.

The pump according to the invention has a low consumption due to its operation in accordance with the physiological heartbeat: an oscillating flow.

The pump according to the invention operates by propulsion: the rhythm is pulsed.

The pump according to the invention makes it possible to limit the surface of contact with the fluid as well as the flow resistance of the turbine. Shear stress on the blood cells is also limited.

With a hollow turbine according to the invention, there is a considerable weight saving, which limits the energy necessary for operation thereof. This also makes it possible to increase the passing flow volume as well as the flow rate.

These advantageous characteristics make it possible to improve the overall comfort of any patient fitted with such a pump.

Provision is advantageously made for the pump according to the invention to operate in a vertical position; with the rotor being arranged vertically, the fluid enters via the inductor, passes through the rotor, and is then outlet at the top via the diffuser and the straightener. Most of the pumps of the prior art operate in a horizontal position. The inlet and outflow capacity allows the pump according to the invention to operate in a vertical position. Such a pump, placed in a left or right ventricle for example, has the advantage of having an inlet and an outlet directly in this ventricle. This makes it possible to avoid the presence of an inlet and/or outlet tube as exists on other devices of the prior art.

The invention claimed is:

1. A turbine for a blood pump, comprising:
a body configured to perform rotational movements;
a hollow central part passing right through the body and intended for passage of blood through the turbine;
at least one vane arranged on an inner wall of the body, in the hollow central part, and configured to cause the blood to flow; and
a rod arranged along a central axis of the turbine so as to reduce backflow of blood, said rod being fixed to one vane, or to the body of the turbine or by one end to an inlet chamber.

2. The turbine according to claim 1, wherein the vane is of a helical type.

3. The turbine according to claim 1, wherein at least one vane is several vanes distributed over the inner wall of said body.

4. The turbine according to claim 1, wherein the at least one vane is constituted by several turns, each successive turn having an increasing winding pitch.

5. The turbine according to claim 1, wherein the hollow central part of the turbine has a cylindrical shape.

6. The turbine according to claim 1, wherein the hollow central part of the turbine has a flared shape, the more open end being arranged downstream in a direction of flow of the blood.

7. The turbine according to claim 1, wherein the hollow central part of the turbine has an oblong shape, a more open end being arranged downstream in a direction of flow of the blood.

8. The turbine according to claim 1, wherein said body has an outer shape of a right cylinder type with a circular cross section.

9. The turbine according to claim 1, wherein permanent magnets are incorporated in said body.

10. The turbine according to claim 1, a radial thickness of the vane is fixed or variable over an entire length between an upstream end and a downstream end of said vane.

11. The turbine according to claim 1, wherein the hollow central part and said at least one vane have a profile of centrifugal type on an upstream side, mixed-flow type in a central part of the turbine, and axial type on a downstream side.

12. The turbine according to claim 11, wherein a first zone of said at least one vane is dimensioned so that the blood reaches a specific speed of between 0 and 1.2 RPM; said first zone being on the upstream side of the vane.

13. The turbine according to claim 11, wherein a second zone of said at least one vane is dimensioned so that the blood reaches a specific speed of between 1 and 2.2 RPM; said second zone being at a level of a middle of the vane.

14. The turbine according to claim 11, wherein a third zone of said at least one vane is dimensioned so that the blood can reach a specific speed greater than 2.2 RPM; said second zone being on the downstream side of the vane.

15. A pump designed for circulation of blood, said pump comprising:
a casing;
a turbine arranged in the casing and configured to perform rotational movements relative to the casing;
the turbine comprising:
a body configured to perform rotational movements;
a hollow central part, passing right through the body and intended for passage of the blood through the turbine;
at least one vane arranged on an inner wall of the body, in the hollow central part, and designed to cause the blood to flow;
a rod arranged along a central axis of the turbine to reduce backflow of the blood, said rod being fixed to one vane, or to the body of the turbine or by one end to an inlet chamber.

16. The pump according to claim 15, wherein the casing and the turbine constitute a part of a brushless motor, the casing having a stator function and the turbine having a rotor function.

17. The pump according to claim 15, wherein the casing has stator windings and the turbine comprises permanent magnets.

18. The pump according to claim 15, wherein a motor is provided external to the turbine and drives the rod which acts as a transmission shaft, said rod being arranged along an axis of rotation of the turbine and solidly connected to the turbine by at least one radial rib.

19. The pump according to claim 18, wherein the transmission shaft is connected at an upstream end and at a downstream end of the vane.

20. The pump according to claim 15, further including:
an inductor equipped with guide blades to make the flow of the blood linear; said inductor being arranged upstream of the turbine with respect to a direction of flow of the blood;
a diffuser equipped with diffusion blades in order to make the flow of blood linear and increase pressure of the blood; said diffuser being arranged downstream of the turbine so as to evacuate the blood outwards from the turbine, converting kinetic energy created by the turbine into potential energy; and
a straightener equipped with straightener blades and an outlet orifice having a diameter less than an inlet diameter of the straightener, the straightener blades directing the blood from the diffuser to the orifice so as to increase speed and give the blood a predefined profile when leaving the orifice.

21. The pump according to claim 20, further including an inlet chamber provided with side openings so that the blood can enter radially, then engage axially towards the inductor.

22. The pump according to claim 21, wherein the inlet chamber has a cylindrical shape comprising, on its upper part downstream of said openings, a receptacle for housing the inductor.

* * * * *